(12) United States Patent
Weissenrieder-Norlin et al.

(10) Patent No.: US 8,419,716 B2
(45) Date of Patent: Apr. 16, 2013

(54) TISSUE STIMULATING DEVICE AND METHOD

(75) Inventors: Anna Weissenrieder-Norlin, Stockholm (SE); Leda Henriquez, Vällingby (SE); Hans Strandberg, Sundbyberg (SE); Eva Harström, Hässelby (SE); Mikael Sjögren, Fjärdhundra (SE); Annika Naeslund, Bromma (SE)

(73) Assignee: St. Jude Medical AB, Jarfalla (SE)

( * ) Notice: Subject to any disclaimer, the term of this patent is extended or adjusted under 35 U.S.C. 154(b) by 478 days.

(21) Appl. No.: 12/445,607

(22) PCT Filed: Oct. 31, 2006

(86) PCT No.: PCT/SE2006/001211
§ 371 (c)(1),
(2), (4) Date: Oct. 25, 2010

(87) PCT Pub. No.: WO2008/054260
PCT Pub. Date: May 8, 2008

(65) Prior Publication Data
US 2011/0040291 A1 Feb. 17, 2011

(51) Int. Cl.
*A61N 1/44* (2006.01)
(52) U.S. Cl.
USPC ....................................................... 604/891.1
(58) Field of Classification Search ............... 604/20, 604/891.1
See application file for complete search history.

(56) References Cited

U.S. PATENT DOCUMENTS

| | | | | |
|---|---|---|---|---|
| 3,275,475 A | * | 9/1966 | Cohn et al. | 429/443 |
| 3,919,723 A | * | 11/1975 | Heimke et al. | 623/23.57 |
| 4,405,311 A | * | 9/1983 | Greatbatch | 604/20 |
| 6,085,118 A | * | 7/2000 | Hirschberg et al. | 607/9 |
| 6,152,882 A | | 11/2000 | Prutchi | |
| 6,567,705 B1 | | 5/2003 | Stokes et al. | |
| 6,665,563 B2 | | 12/2003 | Stokes et al. | |

(Continued)

FOREIGN PATENT DOCUMENTS

| | | |
|---|---|---|
| GB | 2 262 043 | 6/1993 |
| PH | 23540 | 8/1992 |
| WO | WO 02/20087 | 3/2002 |
| WO | WO 2006/018836 | 2/2006 |

OTHER PUBLICATIONS

"pH Regulation of Divalent/Monovalent Ca/K Cation Transport Selectivity by a Macrocyclic Carrier Molecule," Hriciga et al., Proc. Natl. Acad. Sci., vol. 80 (Oct. 1983) pp. 6426-6428.

(Continued)

*Primary Examiner* — Kevin C Sirmons
*Assistant Examiner* — Michael J Anderson

(57) ABSTRACT

A tissue stimulating device that provides a biological stimulation of tissue has a release surface adapted for arrangement adjacent to a tissue to be stimulated. An agent reservoir of the device includes an ionic agent capable of causing a stimulation if present at sufficient high extracellular concentration close to the tissue. An agent releaser is provided in the device for releasing a selected amount of the ionic agent from the agent reservoir to an outside of the release surface at a stimulation occasion for stimulating the tissue. The ionic agent will cause a temporary change in ion permeability of the tissue cell membranes and a depolarization of the tissue cells.

23 Claims, 9 Drawing Sheets

U.S. PATENT DOCUMENTS

| | | |
|---|---|---|
| 6,801,805 B2 | 10/2004 | Stokes et al. |
| 6,832,114 B1 | 12/2004 | Whitehurst et al. |
| 6,849,611 B2 | 2/2005 | Rosen et al. |
| 6,922,586 B2 * | 7/2005 | Davies .................. 600/547 |
| 7,094,201 B1 | 8/2006 | Stokes et al. |
| 2001/0000802 A1 | 5/2001 | Soykan et al. |
| 2003/0074024 A1 | 4/2003 | Stokes et al. |
| 2003/0191500 A1 | 10/2003 | Stokes et al. |
| 2004/0122475 A1 * | 6/2004 | Myrick et al. ............ 607/2 |
| 2004/0152997 A1 * | 8/2004 | Davies .................. 600/547 |
| 2004/0253209 A1 | 12/2004 | Soykan |
| 2005/0203436 A1 * | 9/2005 | Davies .................. 600/547 |
| 2005/0233198 A1 * | 10/2005 | Nuzzo et al. ............. 429/34 |
| 2005/0251221 A1 | 11/2005 | Zdravkovic |
| 2006/0009805 A1 | 1/2006 | Jensen et al. |
| 2007/0093788 A1 * | 4/2007 | Carter .................. 604/890.1 |
| 2008/0154179 A1 * | 6/2008 | Cantor et al. ............ 604/20 |
| 2009/0143761 A1 * | 6/2009 | Cantor et al. ........... 604/501 |

OTHER PUBLICATIONS

"Isolation of a Low Molecular Weight $Ca^{2+}$ Carrier from Calf Heart Inner Mitochondrial Membrane," Jeng et al., Proc. Natl. Acad. Sci., vol. 75 No. 5 (May 1978) pp. 2125-2129.

* cited by examiner

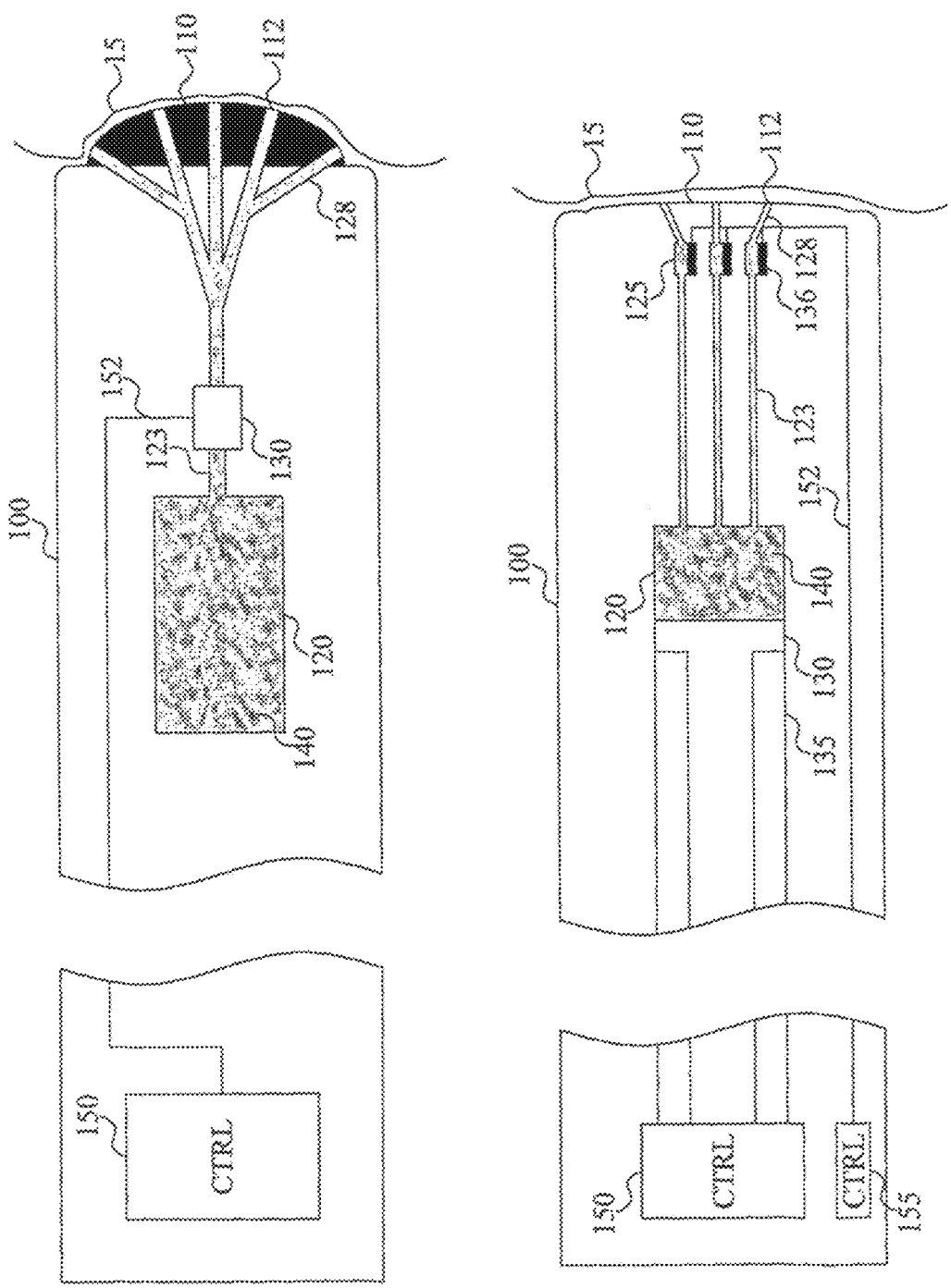

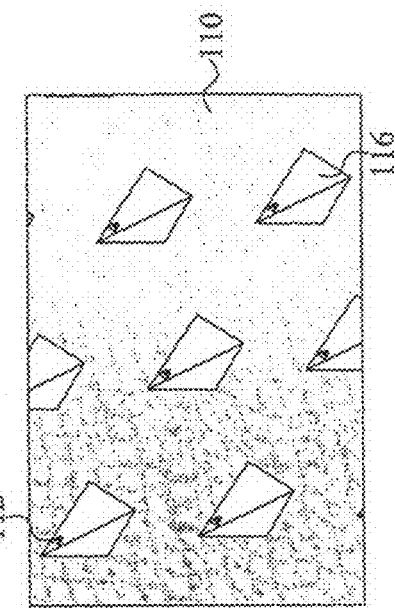
Fig. 7B
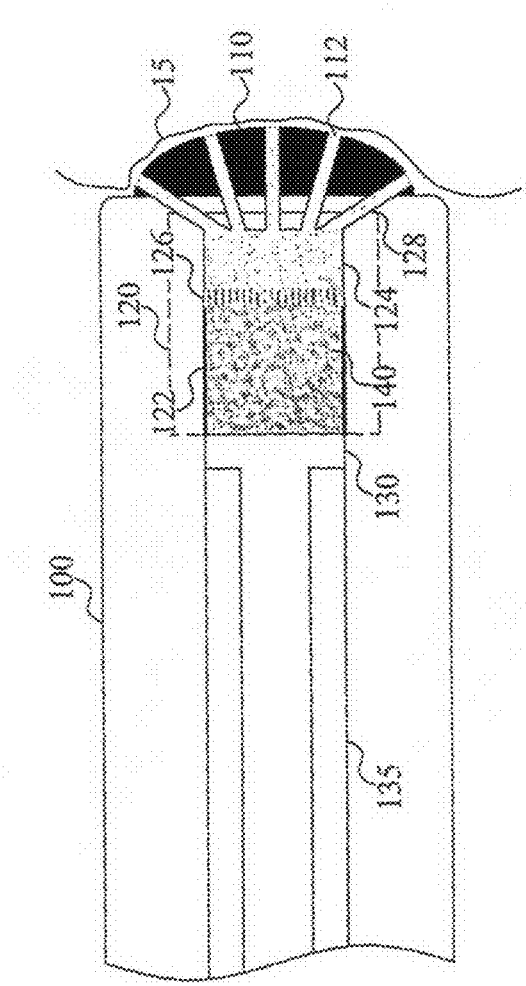
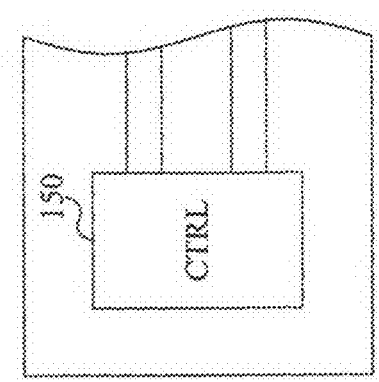
Fig. 6
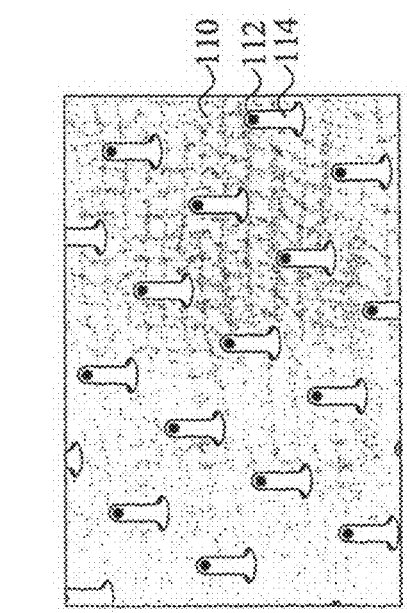
Fig. 7A

TISSUE STIMULATING DEVICE AND METHOD

BACKGROUND OF THE INVENTION

1. Field of the Invention

The present invention relates to methods and devices for tissue stimulations, and more specifically to such methods and devices mimicking natural biological stimulation of tissues.

2. Description of the Prior Art

Artificial activation or stimulation of tissues has been known for centuries. For example, pacemakers, implantable cardioverters and implantable defibrillators are today used for stimulating the heart muscle by applying a current or potential pulse. Such an electrical stimulation pulse is transferred to the heart tissue by an implantable electrode for treating various arrhythmias, such as bradycardia.

Although electrical pacing is readily used and works fairly well it is not a biologically optimal method. The electrode used in the electrical pacing needs a surface potential of at least fifty or even several hundreds times as large as the natural potential needed to induce stimulation. High electrode surface potential in the aqueous biological environment in the patient body is associated with several drawbacks. For example, conventional electrical pacing causes generation of undesirable irreversible reaction products at the electrode-electrolyte interface. In this interface, redox processes involving, among others, proteins in the host body results in reaction products that can have an inflammatory effect and thereby contribute to a local inflammation at the site of the electrode. It is even possible to have gas development and oxidation and release of electrode material, which will cause inflammation and other deleterious conditions in the host body. For example, electrical pacing at potentials below about −0.8 V vs. Ag/AgCl (sat. KCl) causes development of hydrogen gas at the electrode ($H_2O+2e^- \rightarrow H_2+2OH^-$). In addition, the produced hydroxide ions will change the local pH outside the electrode, which have negative effects on the surrounding tissue. Furthermore, depending on the electrode material employed, the produced hydrogen can be absorbed by the electrode. For example, if the electrode comprises a titanium substrate, the absorbed hydrogen will cause brittleness, possibly resulting in crack formation and flaking of the electrode coating. A further negative reaction at the pacing electrode is the production of hydrogen peroxide and hydroxide ions ($O_2+2H_2O+2e^- \rightarrow H_2O_2+2OH^-$). The hydroxide ions negatively affect the local pH and the hydrogen peroxide is a strong oxidizing agent that can damage biological molecules and cells.

There is therefore a need for a more biologically attractive technique for stimulating tissue that is not marred by the problems and disadvantages of electrical pacing described in the foregoing.

SUMMARY OF THE INVENTION

The present invention overcomes these and other drawbacks of the prior art arrangements.

It is a general object of the present invention to provide biologically safe tissue stimulation.

It is another object of the invention to provide a tissue stimulation that mimics the natural biological tissue stimulation in patients.

Yet another object of the invention is to provide tissue stimulation based on a local concentration change of ionic agents in connection with the tissue to be stimulated.

Briefly, the present invention involves a tissue stimulating device that can be used for stimulating or activating an adjacent tissue through the release of an ionic agent close to the tissue to thereby cause a depolarization of the tissue cells and tissue stimulation.

The tissue stimulating device includes a release surface adapted for arrangement adjacent to or in close connection with a tissue to be stimulated. This release surface typically is formed by the end surface or a portion thereof of the tissue stimulating device when having an elongated shape. The stimulation device also has an agent reservoir containing an ionic agent. This reservoir can include the ionic agent in solid form, such as in the form of a salt or in the form of a solid substance capable of decomposing for releasing the ionic agent. Alternatively, or in addition, a reservoir comprising the ionic agent dissolved in a solvent, preferably water, can be used. In such a case, this aqueous agent solution preferably has relatively high agent concentration, e.g. in the range of one or few molars down to one or few tenths of millimolars.

An agent releaser of the stimulating device is in connection with the agent reservoir and arranged for releasing an amount of the ionic agent from the agent reservoir to an outside of the release surface for thereby stimulating the adjacent tissue. The agent releaser is preferably able to release an amount (volume or mass) of the ionic agent sufficient for triggering tissue stimulation within a very short period of time. Thus, the agent release at the release surface can be regarded as instantaneous.

In a preferred implementation, the agent reservoir contains the ionic agent in an aqueous solution. At least one reservoir channel or pipe provides a fluid connection between the agent reservoir and at least one release reservoir. This release reservoir has a considerably smaller internal volume as compared to the agent reservoir. At least one release channel or pipe runs from the release reservoir and ends with its orifice at the release surface. In addition, a piezoelectric element is arranged connected to at least one of the outer walls of the release reservoir. The aqueous solution in the agent reservoir is pressurized with a primary pressure applied in the direction from the reservoir and towards the at least one reservoir channel. The system with the reservoirs and channels will together with the piezoelectric element function as a micro/nano pump, being able to release small volumes of ionic agent solution from the release reservoir through the at least one release channel and to the outside of the release surface upon application of mechanical pulse by the piezoelectric element to release reservoir wall. In addition, by dimensioning the reservoir and release channels so that the flow resistance through the reservoir channel is larger than through the release channel, unintentional solution leakage through the release surface is diminished or prevented.

The invention offers the following advantages:

Mimics the biological tissue stimulation occurring naturally within subject bodies;

Reduces the risk of deleterious processes in connection with the stimulating device;

A simple design consisting of standard elements can be employed; and

Provides instantaneous tissue stimulation.

Other advantages offered by the present invention will be appreciated upon reading of the below description of the embodiments of the invention.

BRIEF DESCRIPTION OF THE DRAWINGS

FIG. 1 illustrates a portion of a tissue stimulating device according to an embodiment of the present invention.

FIG. 2 illustrates a portion of a tissue stimulating device according to another embodiment of the present invention.

FIG. 6 illustrates a portion of a tissue stimulating device according to yet another embodiment of the present invention.

FIGS. 7A and 7B illustrate microstructures useful on a release surface of a tissue stimulating device of the present invention.

DESCRIPTION OF THE PREFERRED EMBODIMENTS

Figure 3:
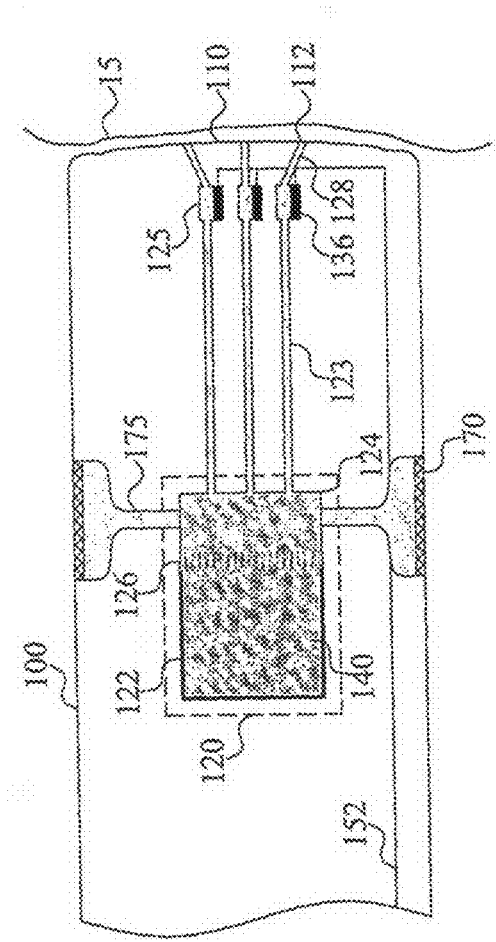
FIG. 3 illustrates a portion of a tissue stimulating device according to a further embodiment of the present invention.

Throughout the drawings, the same reference characters will be used for corresponding or similar elements.

The present invention relates to methods and devices for stimulating and activating tissues using a technique that mimics the natural biological stimulation of these tissues. The methods and devices of the invention result in a local concentration increase of an ionic agent in the vicinity of a tissue. This local concentration increase will trigger an activation process in cells of the tissue resulting in tissue stimulation.

The expression "stimulation" is used herein to denote a stimulation or activation of a tissue "artificially" induced by the methods and devices of the present invention. This artificially induced stimulation, however, mimics the biological stimulation that occurs naturally in certain healthy tissues. Generally, stimulation induced by the local increase in the ionic agent concentration of the invention results in a depolarization of cells in the tissue. In other words, the concentration increase will affect the permeability and flow of different ions through the cell membranes in these tissue cells. This permeability change is a result of an induced opening and/or closing of ion channels present in the cell membranes. The ion channel opening causes an influx or outflux of certain ions specific for these ion channels into or out from the cells. This ion flow may in turn induce opening and subsequent inactivation and closure of other ion channel types having specificity for other ions present inside or outside of the cells. The net result will be an initial (temporary) depolarization of the cells. This cell depolarization will generally spread throughout the tissue cells and thereby causing tissue stimulation.

For example, in heart tissue the local increase of ionic agent of the present invention will induce an opening of fast voltage-gated sodium channels and slow calcium channels. The opening of the fast sodium channels causes an influx of sodium ions and depolarization of the cells (generation of an action potential). These sodium channels are fast in terms of inactivating or closing rapidly after opening, typically within only a few 10 000ths of a second. The slower calcium channels remain open for a comparatively longer period of time and account for a depolarization plateau. At the end of the plateau period, potassium channels open causing an outflow of potassium ions from the cells and a rapid repolarization of the cells to the resting membrane potential.

A corresponding stimulation also occurs in other tissue types, such as skeletal muscle and nerve tissue, though the types of ion channels involved, their gating mechanism and opening/closure/inactivation time may differ. For example, no depolarization plateau is generally present following the depolarization spike in skeletal muscle.

The present invention can be applied to and used for stimulating different tissue types that naturally can be subject to stimulation in a healthy subject. Non-limiting examples include heart (muscle) tissue; other types of muscle tissue, such as skeletal and smooth muscles; nerve tissue; Purkinje fibers; sinus node; A-V node; etc. Actually any tissue having cells that can be depolarized by a temporary increase in extracellular concentration of an ionic agent or substance can be stimulated according to the present invention.

The ionic agent of the present invention can be any biocompatible ionic substance or composition that is capable of affecting the permeability of cell membranes to different ions to generate an ion flow over the membranes and a cell depolarization. In a preferred embodiment, the ionic agent is a biocompatible mono- or multivalent (such as divalent or trivalent) ion, more preferable a monovalent or divalent cation and most preferably a monovalent cation. Preferred monovalent cations can be found among cations of group 1 elements in the period table of the elements. Thus, sodium ($Na^+$), potassium ($K^+$), rubidium ($Rb^+$), cesium ($Cs^+$) and francium ($Fr^+$) ions can be used according to the present invention. A currently preferred ionic agent is potassium ions. Preferred divalent cations that can be used according to the present invention include magnesium ($Mg^{2+}$) and calcium ($Ca^{2+}$) ions.

It is anticipated by the present invention that the ionic agent can be a mixture of different ions, for example a mixture of potassium and calcium ions. Therefore, the expression ionic agent refers to any single ion or ionic substance capable of causing a tissue stimulation when present at an adequate amount in the vicinity of the tissue cells, or a mixture or composition comprising multiple different such ions or ionic substances.

The ionic agent is typically provided in the form of a salt with a selected counter ion. This counter ion should of course also be biocompatible and not cause any local or systemic lesions to the patient body at the concentration levels used by the invention. For example, if potassium or another cation is employed as ionic agent of the invention, suitable counter ions include chloride ($Cl^-$) and acetate ($CH_3COO^-$) ions.

The salt with the ionic agent of the invention can be provided in the tissue stimulating device in solid form or in the form of a solution with a biocompatible solvent, preferably water. In the latter case, the aqueous solution preferably has a high concentration of the ionic agent. As a consequence, the solution can be a saturated saline solution, including the ionic agent in a highest achievable concentration. However, as the solubility of preferred ionic agents, such as potassium chloride, in water is very high, also sub-saturation solutions can be used according to the present invention. The reason for using a high concentration solution is that only a very small (minute) volume of the concentrated solution is needed per stimulation occasion as compared to employing a low concentration solution.

The usage of the ionic agent in solid form (as a salt) is preferred in terms of size aspects. Thus, a considerable large amount of the ionic agent can be included in the tissue stimulating device if provided in solid form. However, releasing a selected amount of the solid ionic agent may be technically more complex than releasing a selected volume of the ionic agent solution. The present invention therefore also teaches a combined usage of solid ionic agent and an ionic agent solution. As will be further disclosed herein, the ionic agent in solid form can then be regarded as a bulk or store source from which portions of the ionic agent is transferred to the solution to thereby prevent depletion of the ionic agent from the solution and a too large lowering of the agent concentration of the solution.

The tissue stimulating device may also include an agent reservoir that comprises a material that is degraded to form the ionic agent. In such a case, this ionic-agent-containing material can be in solid form and degrades in a determined rate to replenish ionic agent in an aqueous agent solution. An example of such a material is the above mentioned KCl salt that can be degraded or decomposed into potassium and chloride ions of a solution.

An aspect of the present invention relates to a tissue stimulating device useful for artificially inducing a stimulation of a tissue, for example, in a subject having a disease or medical condition requiring artificial tissue stimulation or for performing in vivo stimulation of explanted or cultured tissue. An embodiment of the tissue stimulating device 100 is illustrated in FIG. 1. The tissue stimulating device 100 generally includes an agent reservoir 120 comprising an ionic agent 140 employed for the tissue stimulation induction. In this embodiment, the agent reservoir 120 comprises the ionic agent 140 in the form of a (high concentration) solution. An agent releaser of the stimulating device 100 in the form of a pump arrangement 130 is arranged for releasing a selected amount of the ionic agent 140 from the agent reservoir 120 to an outside of a release surface 110 of the stimulating device 100. A reservoir channel or pipe 123 connects the pump arrangement 130 with the agent reservoir 140. The pumped amount of agent solution is released through one or more release channels or pipes 128, schematically illustrated in the form of multiple branched off channels 128 ending with their orifices 112 in the release surface 110. This release surface 110 is adapted for arrangement adjacent to or in connection with a tissue 15 to be stimulated. The release of the selected amount of the ionic agent 140 at the outside of the release surface 110 causes a local, instantaneous but temporary increase in the extracellular concentration of this ionic agent 140 close to cells in the tissue 15. This local extracellular ionic agent concentration causes the stimulation of the tissue 15 through a depolarization of the tissue cells.

The pump 130 can be any arrangement capable of drawing off a selected volume of the ionic agent 140 from the agent reservoir 120 and releasing the solution volume through the release channel(s) to the outside of the release surface 110. As the internal space of the tissue stimulating device 100 is limited, pump arrangements 130 having an overall small size, such as micro or nano pumps, are preferred. A further preferred requisite is that the pumping action of the pump arrangement 130 is fast, implying that the selected pumped volume will substantially instantaneously be released at the interface between the release surface 110 and the tissue 15 at a stimulation occasion. In other words, the pumping action should not gradually/continuously pump out the selected amount so that the amount of the ionic agent 140 at the outside of the release surface 110 increases slowly. However, as only small volumes (in the order of µl or nl) of the ionic agent solution 140 are generally needed per stimulation occasion, this is typically no problem for the available micro pump solutions that can be used according to the invention.

The timing of agent pumping and optionally the amount of agent solution 140 that is being pumped by the pump arrangement 130 is controlled by a release controller 150 connected by a control wire 152 to the pump arrangement 130. At a stimulation occasion, the release controller 150 generates and forwards, through the control wire 152, a release (voltage) signal to the pump arrangement 130, causing the pump 130 to draw a selected volume of the agent solution 140 from the reservoir 120 and releasing it through the release channels 128 to the outside of the release surface 110.

In a particular implementation, the release controller 150 can, in addition to the release timing, also control the volume that is pumped by the pump arrangement 130 for each stimulation occasion. This can be useful since the pumping then can compensate for variations in the concentration of the ionic agent 140 in the aqueous solvent. Correspondingly, different tissues may require different amounts of the ionic agent 140 for triggering stimulation. In such a case, the release controller 150 signals the pumping arrangement 130 to pump a larger or smaller volume of the agent solution 140 from the reservoir 120.

The tissue stimulating device 100 may include one agent reservoir 120 and one pumping arrangement 130 as illustrated in the figure. In an alternative embodiment, the device 100 comprises multiple, i.e. at least two, agent reservoirs 120, each being connected to at least one pumping arrangement 130 for drawing selected volumes of the ionic agent solution. In this embodiment, the respective reservoir channels 123 of the agent reservoirs 120 can merge into a single channel to which a pumping arrangement 130 is arranged. Thus, a single pumping arrangement 130 is used for pumping solution volumes from multiple agent reservoirs 120. Alternatively, each agent reservoir 120 (if more than one) can be equipped with multiple reservoir outlet channels 123 and pumping arrangements 130.

In similarity to the discussion above, the release channel 128 can branch off to form a tree-like structure as in the figure to thereby provide orifices or outlets 112 all over the release surface 110. If however multiple pumping arrangements 130 are arranged in the stimulating device 100 non-branching channels 128 can be used and still providing an orifice covering over substantially the whole surface 110.

In order to prevent unintentional leakage of agent solution 140 from the release channels 128 to the outside of the release surface 110 and/or preventing body fluids from entering the release channels 128, the orifices of the channels 128 can be equipped with check valves. In such a case, the pumping arrangement 130 can pump out portions of the agent solution 120 through the valves. However, when the pumping arrangement 130 is idle, the valves are closed, effectively preventing leakage out from and into the release channels 128.

FIG. 2 is a schematic illustration of a portion of a tissue stimulating device 100 according to another embodiment of the present invention. In this embodiment, the agent reservoir and release system comprises at least one reservoir 120 comprising the ionic agent, typically in a (high concentration) solution. The system further includes at least one (non-limitedly illustrated by three in the figure) release reservoir 125 connected to the agent reservoir 120 through a reservoir channel or pipe (first transport channel) 123. The internal volume of the agent reservoir 120 is comparatively considerably larger than the internal volume of a release reservoir 125. In this way, the agent reservoir 120 can be regarded as a bulk store of the ionic agent 140 while the release reservoir(s) 125 house(s) a much smaller amount of the ionic agent to be ejected for stimulating the adjacent tissue 15. The release reservoirs 125 are in turn connected through release channels or pipes (second transport channel) 128 to the release surface 110, in which the channel orifices 112 are provided.

Instead of employing traditional (micro) pumps, this embodiment utilizes a pressure arrangement 130, piezoelectric elements 136 and reservoir and release channels 123, 128 for releasing selected volumes of the ionic agent solution.

The pressure arrangement 130 can be realized with any arrangement capable of exerting a primary fluid pressure on the solution in the agent reservoir 120 towards the release channels 123. In FIG. 2, the pressure arrangement 130 is exemplified by a piston 130 running in an adapted cylinder or bore 135 of the stimulating device 100. Thus, the pressure arrangement 130 operates similar to a syringe pushing ionic agent solution into the reservoir channels 123. The piston 130 is controlled by a piston controller 150 that can be in the form of a piston motor pushing the piston 130 in the cylinder 135. In a preferred embodiment, the piston controller 150 and piston 130 mutually operate for exerting a continuous, consistent, non-varying fluid pressure. This applied fluid pressure guarantees that the release reservoirs 125 become replenished with the ionic agent 140 containing solution from the reservoir 120 after tissue stimulation occasions.

The piezoelectric elements 136 are connected to the release reservoirs 125 and are arranged for applying a mechanical pulse on the reservoirs 125 at the release moment. This applied mechanical pulse causes a reversible deformation (squeezing) of the reservoir walls and the ejection of a small volume of the agent solution contained therein. Due to the fluid pressure exerted by the piston arrangement 130, the mechanical pulse will eject the solution volume through the release channels 128 and to the outside of the release surface 110. The operation of these piezoelectric elements 136 will therefore be similar to a micro/nano pump in terms of being able to pump defined small volumes of the ionic agent solution out of the tissue stimulating device 100. In this context, a single piezoelectric element 136 can be arranged connected to a wall per release reservoir 125. Alternatively, multiple piezoelectric elements 136 are connected to each reservoir 125. In such a case, the elements 136 are preferably mutually arranged on each side of the reservoir 125. It is also possible that a single piezoelectric element 136 is connected to multiple reservoirs 125.

The dimensions (inner diameter and length) of the reservoir channels 123 and the release channels 128 and the respective number of these channels 123, 128 are preferably selected to obtain a ratio of total flow resistance between the reservoir channels 123 and the release channels 128 of about 10:1 to about 100 000:1. In operation simulations of the tissue stimulating device 100 of FIG. 2, a flow resistance ratio of 100:1 have been given favorable results in terms of leakage prevention and instantaneous solution release.

The piezoelectric elements 136 are controlled by a release controller 155, which is electrically connected to the elements 136 by a control wire 152. At a stimulating occasion, the release controller 155 applies a voltage to the piezoelectric elements 136 causing a mechanical pulse that reversible deforms or squeezes the reservoirs 125 and ejects controlled amount of the agent solution. The release controller 155 therefore controls the time instants of stimulation by applying a drive voltage onto the piezoelectric elements 136 but also the length of the mechanical pulse generated by the piezoelectric elements 136. In most practical implementations a pulse length of a few tenths up to a few tens of milliseconds is adequate. For example, in stimulation experiments a pulse length of 1 ms has been successfully employed.

It is anticipated by the present invention that other arrangements and elements besides piezoelectric elements can be used for applying a short mechanical pulse to the release reservoir walls.

FIG. 3 is a schematic illustration of a portion of a tissue stimulating device 100 according to a further embodiment of the present invention. This embodiment also employs a system of at least one reservoir channel 123 providing a fluid connection between a solution agent reservoir 124 and at least one release reservoir 125 and at least one release channel 128 as output channel of the release reservoir(s) 125.

The tissue stimulating device 100 comprises an agent reservoir 120 including two different reservoirs, a solid agent reservoir 122 and an agent solution reservoir 124. The solid agent reservoir 122 contains, as its name suggest, the ionic agent 140 of the invention in solid form, typically as a salt, e.g. KCl. The agent solution reservoir 124 in contrast contains the ionic agent 140 in a solution, preferably a high concentration solution, including a saturated solution.

The two reservoirs 122, 124 are separated by a solid-solution interface 126. In a first embodiment, the agent solution in the agent solution reservoir 124 is a saturated solution or at least near saturation. In such a case, the interface 126 can be realized by a meshed structure that allows for continuous contact between the solid ionic agent 140 and the solution. Furthermore, the solution reservoir 124 is equipped with at least one re-fill channel 175 that is used for replacing ejected solution volumes with (body) fluid/liquid taken from the surrounding environment. This re-fill channel 175 is then equipped with a semi-permeable membrane 170 that is permeable to water but impermeable to the ionic agent in the solution reservoir 124 and preferably other ions, molecules and cells present in the external body fluid environment. As the solution reservoir 124 becomes re-filled with fluid, the concentration of the ionic agent 140 will decrease. However, since the solution in the solution reservoir 124 is in contact with the solid ionic agent 140 containing material of the solid reservoir 122 through the interface 126, ionic agent 140 will be dissolved in the solution and thereby increasing the agent concentration, preferably back to the original concentration level before solution ejection.

In this embodiment, no active pressurizing equipment is required since the osmotic pressure over the semi-permeable membrane 170 will cause an influx of body fluid (water) through the membrane 170 and into the solution reservoir 124 through the re-fill channel(s) 165. This osmotic pressure arises due to the high concentration of the ionic agent 140 in the solution reservoir 124 and the comparatively vastly lower agent concentration in the body fluids outside of the membrane 170. This arising osmotic pressure is high enough to press ionic agent solution through the at least one reservoir channel 123 and into the release reservoir(s) 125 as this/these need(s) to be refilled after a stimulation action. If the solid agent reservoir 122 comprises the ionic agent 140 in the form of KCl and the solution agent reservoir 124 correspondingly comprises a concentrated (possibly saturated) KCl solution, the osmotic pressure can be in the order of 120 atm. This high pressure will cause outflow, preferably continuous outflow, of concentrated ionic agent solution from the solution reservoir 124, through the reservoir channel(s) 123 and into the smaller release reservoir(s) 125.

The agent reservoir 120 (solution agent reservoir 124 and solid agent reservoir 122) is preferably mechanically rigid to prevent any volume/wall expansion due to the osmotic pressure and influx of fluid through the re-fill channel(s) 165. In contrast, the release reservoirs 125 are preferably expandable or comprise an expandable element. This can be realized by elastically or expandably attaching the piezoelectric elements 136 to the release reservoirs 125 and/or having at least one expandable wall or wall portion per reservoir 125.

As the piezoelectric elements 136 are electrically excited by the release controller 155 through the control wire 152, a defined pressure rise is obtained, causing a temporary outflow of ionic agent solution from the release reservoirs 125 and the release channels 128 to the outside of the release surface 110. Once the excitation is ended, a continuous declining (temporary) inflow of fluid through channel orifices in the release surface 110 is present.

The dimensioning of the reservoir channels 123 (length and inner diameter) is preferably selected to result, with the added (osmotic or generated) drive pressure, in a continuous flow of about 0.01 to 10 µg ionic agent 140 per second, preferably of about 0.2 to 1 µg/s if the ionic agent solution is a KCl solution. In the latter preferred case, this corresponds to a flow of about 0.5 to 3 nl/s, depending on the actual concentration of the KCl solution.

The flow resistance in the reservoir channels or capillaries 123 effectively prevents inflow of solution from the release reservoirs 125 to the solution reservoir 126 at a solution ejection occasion. The corresponding flow resistance (and thereby the dimensions, i.e. length and inner diameters) of the release channels 128 is preferably in the range of 1/100 to 1/1000 of the flow resistance of reservoir channels 123.

The internal volumes of the release channels 128, the flow resistance through these channels 128 and the internal volume of the release reservoirs 125 collectively define the characteristics of the temporary inflow of fluid after ejection of a defined volume at a tissue stimulating occasion. These characteristics can be represented by a time duration constant of the return flow. In simulation experiments a time duration constant of about 250 to 300 ms has been obtained as the duration time of the return flow.

In a preferred implementation of the invention, the internal volume of the release reservoirs 125 is selected to be at least about 10 times larger than the volume of ionic agent solution ejected per tissue stimulation occasion. The volume is preferably at least 100 times, and more preferably in the order of about 1000 times larger than the ejected solution volume.

The volume of ejected solution volume from the release channels 125 and therefore from the tissue stimulating device 100 can be controlled by the pulse amplitude and pulse duration of the electrical excitation pulse applied to the piezoelectric elements 136. In this way the ejected volume can be controlled from about 0.1 nl to about 10 µl, preferably in the interval of 1 to 100 nl, depending on the concentration of the ionic agent in the solution.

The operation of the remaining units of the tissue stimulating device is similar to FIG. 2 and is not repeated herein.

Figure 4:
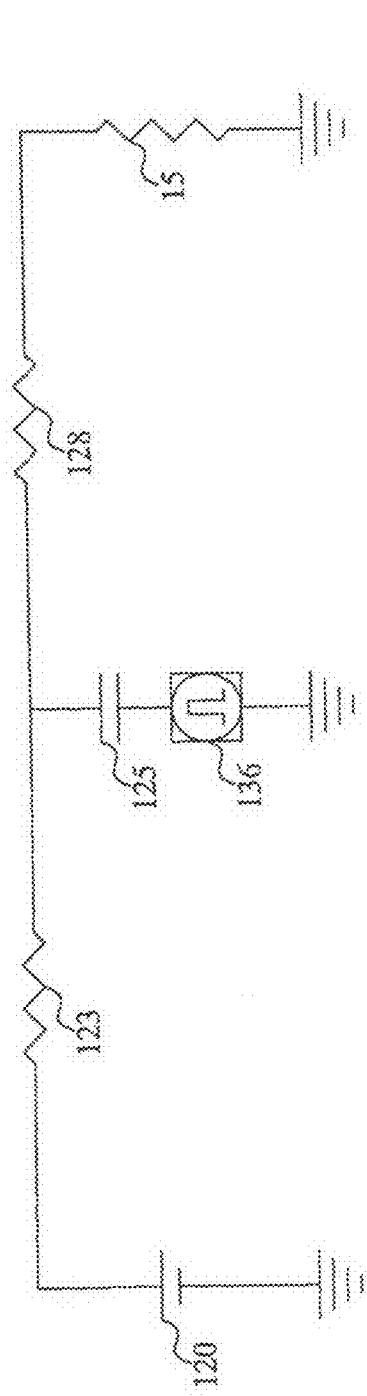
FIG. 4 is a drawing schematically illustrating the operation of the agent reservoir and releasing system of the tissue stimulating device in FIGS. 2 and 3.

FIG. 4 is a schematic electric model of the reservoir and release system of the tissue stimulating device in FIGS. 2 and 3. The large volume agent reservoir can be exemplified with a voltage source 120 charging a capacitor 125 that represents the release reservoir. These two elements 120, 125 are connected through a resistor 123 having a high resistance. The high resistance resistor 123 represents the long, narrow reservoir channels. A corresponding low resistance resistor 128 connects the capacitor 125 to a load 15 representing the tissue to be stimulated. The resistor 128 is an electrical representation of the short release channels. The mechanical pulse of the piezoelectric element will in this electrical model be generated by an electric pulse generator 136.

Figure 5:
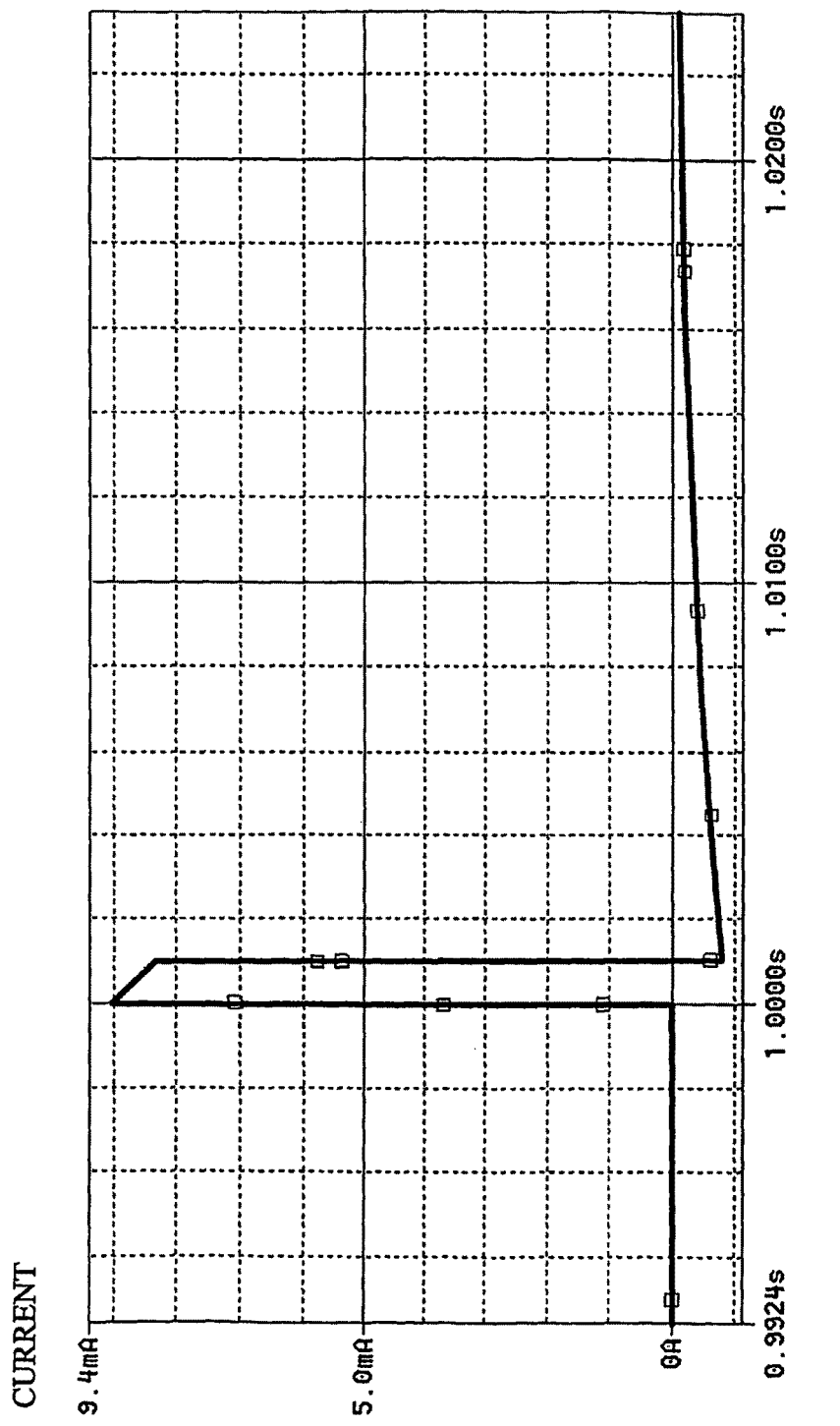
FIG. 5 is a diagram of an operation simulation of the tissue stimulating device of FIGS. 2 and 3.

An electronic (P-spice) simulation of the operation of the electrical circuit of FIG. 4 representing the operation of the tissue stimulating device of FIGS. 2 and 3 has been performed. In this simulation, the voltage source 120 was a 5 V battery, the agent reservoir representing resistor 123 had a 10 kΩ resistance, the release reservoir representing resistor 128 had a 100Ω resistance, the tissue representing resistor 15 had a 10Ω resistance, the capacitor 125 had a capacitance of 100 µF and the pulse generator stepped between the voltage levels 0 V and 1 V with a pulse length of 1 ms. The electrical current through the tissue representing resistor 15, which represents the flow of the ionic agent solution out of the release surface, was monitored. The diagram of FIG. 5 illustrates this monitored current.

As the voltage pulse is applied by the pulse generator the current over the release resistance increases instantaneously in a spike-like manner. Once the pulse is over, a small return current is present for about 150 ms before the current is returned to the level of rest.

This electrical simulation illustrates that when the release controller 155 triggers a mechanical pulse at the piezoelectric elements 136, this pulse increases the pressure inside the release reservoirs 125 causing flow of ionic agent solution out from the reservoirs 125 and into release channels 128 (due to the primary pressure exerted by the piston arrangement 130 or osmotic pressure). Once the piezoelectric elements 136 returns to the state of rest, an initial and temporary underpressure is developed inside the release reservoirs 136, causing a temporary return flow of fluid/solution into the reservoirs 136 (unless check valves are provided at the channel openings 112). The combination of the solution flow from the agent reservoir 120 and the small return flow following a solution ejection guarantees that a correct solution level is present in the release reservoirs 125.

The system with the pressurized larger volume agent reservoir 120 connected to the small volume release reservoir 125 with a reservoir channel 123 exerting a high flow resistance and a release channel 128 with low flow resistance allows for efficient pumping out selected volumes of the solution 140 in the release reservoir 125 upon application of a mechanical pulse onto the release reservoir 125. In addition, the system provides refilling of the release reservoir 125 with solution from the agent reservoir 120 and external fluid/solution after an ejection occasion. Continuous leakage of the solution 120 from the release reservoir 125 is also prevented or kept at a low level. As a consequence, this embodiment could be used without any check valves in the end of the release channels 128.

Consistent with the embodiment disclosed in FIG. 1, the tissue stimulating device 100 of FIG. 2 or 3 can be equipped with one or more agent reservoirs 120, each being connected to one or more release reservoirs 125 by one or more reservoir channels 123. In addition, release channels 128 branching off to form a tree-like structure can be used to allow for several release outlets all over the release surface 110.

FIG. 6 is a schematic illustration of a portion of a tissue stimulating device 100 according a further embodiment of the present invention. In this embodiment, the agent reservoir 120 comprises two different reservoirs, a solid agent reservoir 122 and an agent solution reservoir 124. From the agent solution reservoir 124 one or more release channels or pipes 128 are branching, ending in the release surface 110. In a preferred implementation, multiple such release channels 128 are used for providing release openings or orifices 112 over at least a part of the release surface 110.

The two reservoirs 122, 124 are separated by a solid-solution interface 126. In a first embodiment, the agent solution in the agent solution reservoir 124 is a saturated solution or at least near saturation. In such a case, the interface 126 can be realized by a meshed structure that allows for continuous contact between the solid ionic agent 140 and the solution. Furthermore, the solution reservoir 124 is equipped with a membrane-equipped re-fill channel (not illustrated) that is used for replacing ejected solution volumes with (body) fluid taken from the surrounding environment, as was described above in connection with FIG. 3.

In an alternative implementation, the solid-solution interface 126 is in the form of at least one, preferably a matrix or grid of multiple, check valves mounted in a back panel. Portions of solid ionic agent 140 can then be pushed through the at least one check valve in the interface 126, for example by means of a piston arrangement 130. The check valves also prevent the solution in the solution reservoir 124 from penetrating into solid reservoir 122.

In the embodiment illustrated in FIG. 6, a piston arrangement 130 running in a dedicated cylinder or bore 135 is employed for pushing a selected volume of ionic agent solution through the release channel(s) 128 and out to the outside of the release surface 110, where the ionic agent 140 will cause a stimulation to the adjacent tissue 15. The timing and control of the inwards movement of the piston 130 is performed by a piston controller 150. This piston controller 150 then comprises both the arrangement for performing the actual piston movement, for example in the form of a piston motor, and the control function required for determining how much the piston 130 is to moved towards the agent reservoirs 122, 124.

As was described in the foregoing, the outlet openings 112 of the release channels 128 are preferably equipped with check valves for preventing unintentional solution leakage from and/or body fluid ingress into the channels 128.

The release surface 110 of the tissue stimulating device 100 can be any flat, convex, concave or irregular surface having at least one channel outlet. In order to minimize the distance between the surface 110 and the tissue to be stimulated 15 a flat or convex surface geometry is generally preferred. The size of the release surface 110 is preferably selected to match a selected area of the tissue 15 to be stimulated. As the cell depolarization caused by releasing the ionic agent 140 of the invention at the surface-tissue interface generally is spread throughout the stimulable part of the tissue 15 once a portion of the tissue cells have been depolarized, the release surface 110 merely have to cover a small portion of the tissue 15 to be stimulated. In most practical implementations, a total surface area of one or few tenths of square millimeters up to one or few tens of square millimeters is suitable. For example, a total surface area of about a few square millimeters can be adequate for most tissue stimulation applications. However, if stimulation of relatively small tissues is desired, such as nerve tissue stimulation, even smaller release surfaces 110 can be used.

The channel orifices 112 of the release channels 128 preferably cover a substantial portion of the release surface 110. The channels 128 can be mutually arranged to form a matrix, grid or other regular or irregular pattern of orifices 112 in the surface 110. It is also possible to use micro-structures connected to the channel orifices 112 as is illustrated in FIGS. 7A and 7B. In FIG. 7A, the release channels end in micro needles 114 arranged over the release surface 110. Each such micro needle 114 has a small opening 112, through which the ionic agent solution is released. In FIG. 7B, micro spikes 116 with small openings 112 have been employed instead of micro needles.

The micro needles and micro spikes disclosed in FIGS. 7A and 7B can be provided, for example, from Silex Microsystems that produces micro-electromechanical systems. These micro-structures can be used for facilitating correct delivery of the ionic agent to the vicinity of the tissue to be stimulated. In other words, the micro-structures enable distribution of the ionic agent over a desired surface of a stimulable tissue. In addition, the structures make sure that the ionic agent is released very close to the tissue to prevent the agent from dispersing before stimulation is triggered.

Figure 8:
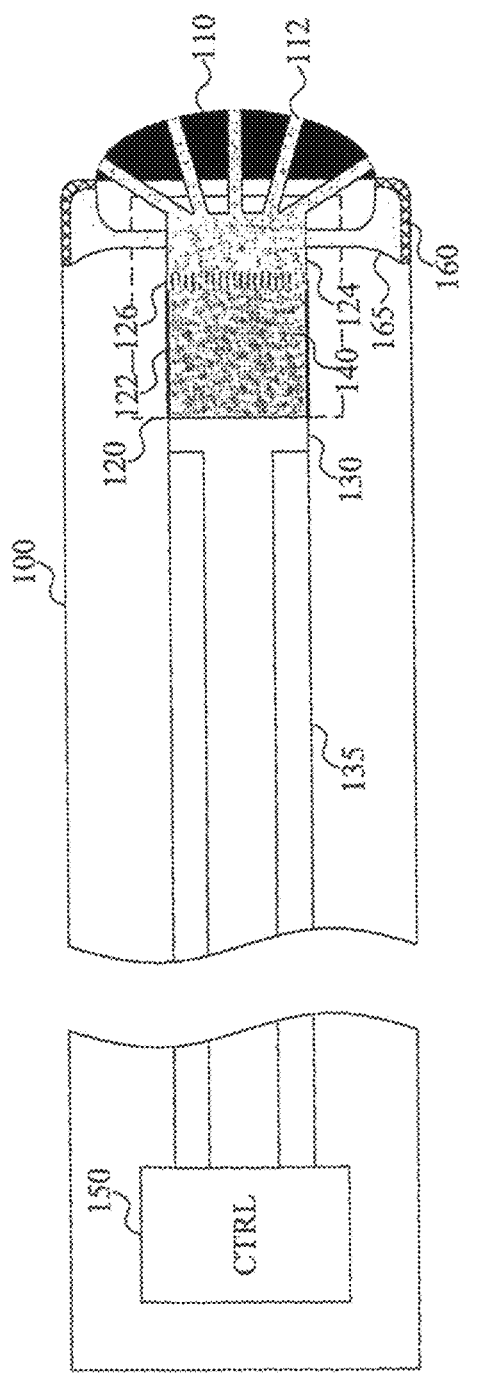
FIG. 8 illustrates a portion of a tissue stimulating device equipped with ion enriching functionality.

The tissue stimulating device 100 of the present invention may, as is illustrated in FIG. 8, also be equipped with an arrangement 160 for enriching ionic agents from the surrounding environment, such as from body fluid (blood) present outside of the stimulating device 100. This means that ionic agent 140 released, at a stimulation occasion, from the tissue stimulating device 100 and/or ionic agent 140 naturally occurring in the surrounding body fluids can be captured and returned to ionic agent solution in the agent reservoir 120. As a consequence, the total service life of the tissue stimulating device 100 may be increased since the stimulating device 100 can be operated over a comparatively longer period of time before the ionic agent 140 is depleted in the reservoir 120 as compared to a corresponding tissue stimulating device 100 without any agent enriching arrangement 160. Alternatively, usage of the enriching arrangement 160 implies that smaller bulk amounts of the ionic agent 140 is needed in the reservoir 120.

The enriching arrangement 160 is arranged on the outer surface of the tissue stimulating device 100, preferably close to the release surface 110 or indeed in the release surface 110. The arrangement 160 may then capture ionic agent 140 released from the channel openings 112 at a stimulation occasion before a substantial amount of the ionic agent 140 dissociates away from the release site. For example, if the release surface 110 constitutes the end surface of a pen-shaped stimulating device 100, the enriching arrangement 160 may advantageous cover at least a portion of the envelope area close to the device end. It is evident to the person skilled in the art that the larger area the enriching arrangement 160 covers the more ionic agent 140 can be captured from the surrounding environment.

The enriching arrangement 160 is connected through one or more conduits 165 to the agent reservoir 120, preferably the solution agent reservoir 124 if both a solid and a solution agent reservoir 122, 124 are present.

In a preferred implementation, the enriching arrangement is in the form of an ion exchange membrane or filter 160 arranged on the outer surface of the tissue stimulating device 100. The ion exchange membrane 160 may be a matrix containing an ion exchange resin, zeolite, montmorillonite, clay, humus or other material.

An example of ion exchange membrane is SELEMION™ that provides both anion exchange and cation exchange membranes. These membranes are films which are 100 to 200 μm in thickness, having ion passing pores of a few Angstrom in diameter, in which fixed ions of anion or cation are introduced. The ionic agent of the invention can then be enriched using such a SELEMION™ membrane 160 by utilizing e.g. electric energy for providing the driving action forcing the ionic agent 140 through the membrane and into the conduit 165. Other ion exchange membranes include PC-SK and PC-SA from PCA and NAFION® (trade name for sulfonated tetrafluoroethylene copolymer).

In an alternative embodiment of the tissue stimulating device, the ion exchange membrane can constitute the agent releaser and the release surface. In such a case, the tissue stimulating device comprises an agent reservoir or multiple agent reservoirs, such a solid and aqueous agent reservoir. The (aqueous) agent reservoir is connected, either directly or through at least one release channel, to the ion exchange membrane. At a tissue stimulating occasion, the membrane allows diffusion of the ionic agent from the reservoir/channel through the membrane and to its outside. In such a case, the diffusion or transport of the ionic agent through the ion exchange membrane is controllable by a release controller. In a first simple implementation, this release controller can be in form of a reversible obstruction on the release channel, preventing the ionic agents in the reservoir from reaching the ion exchange membrane. At a stimulation occasion, the reversible obstruction is removed from the channel causing the ionic agent to reach and pass through the ion exchange membrane. It is anticipated by the invention that other types of release controller arrangements besides mechanical can be used in this alternative embodiment. For example, the release controller can include an electrode for applying an electrical driving potential forcing the ionic agent of the invention to be released through the ion exchange membrane so that it there outside can stimulate a tissue.

The teachings of the above-presented embodiments of the tissue stimulating device may be combined. For example, a double-reservoir system with both a solid and solution reservoir of FIGS. 3, 6 and 8 can be used together with the stimulating devices disclosed in FIGS. 1 and 2. Correspondingly, usage of only one or more solution reservoirs as in FIGS. 1 and 2 can also be applied to the stimulating devices of FIGS. 6 and 8. An enriching arrangement as in FIG. 8 can also be used in the device embodiments disclosed in FIGS. 1, 2, 3 and 6.

Figure 9:
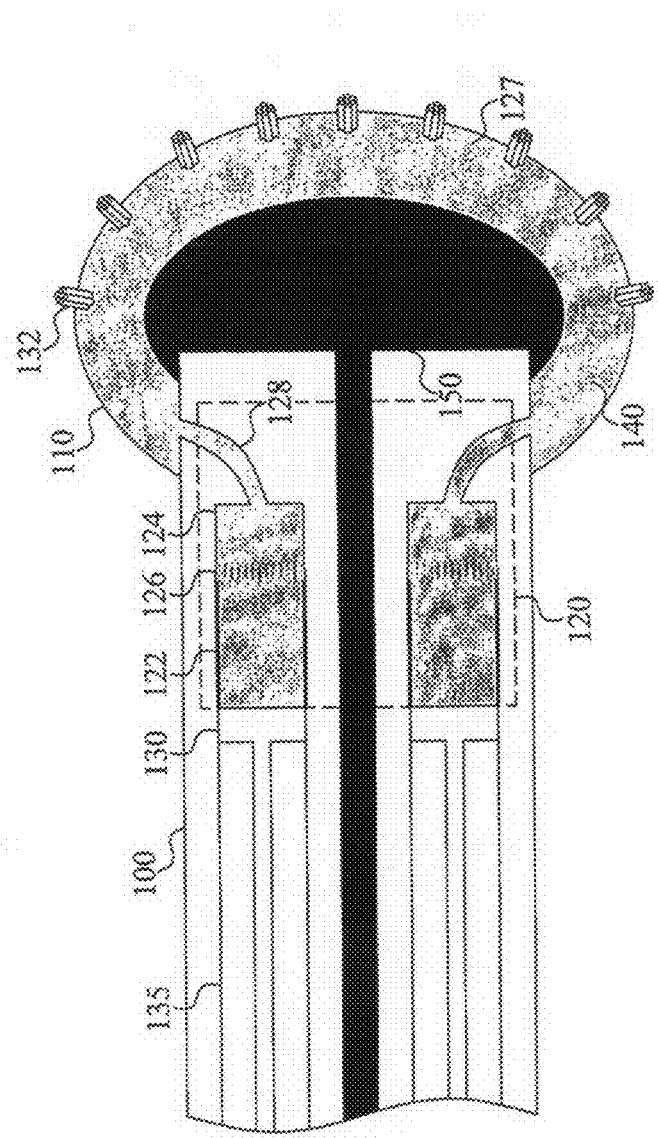
FIG. 9 illustrates a portion of a tissue stimulating device according to yet a further embodiment of the present invention.

FIG. 9 is a schematic illustration of an end portion of a tissue stimulating device 100 according to still another embodiment of the present invention. In this embodiment, the release surface 110 consists of a membrane structure, into which channels 132 are inserted.

The membrane can be made by phospholipids or other amphipathic molecules forming a bilayer. Thus, this membrane is similar to the cell membranes in its structure. Other types of membranes, including different, possibly modified, self-assembling mono- or bilayers can also be used according to the invention.

Multiple ionic agent specific channels 132 are provided inserted or embedded in the membrane. The membrane structure encloses a space 127 containing a (aqueous) ionic agent solution 140. This space 127 is furthermore in fluid connection with the solution agent reservoir 124 through a release channel or pipe 128 or could be regarded as constituting a part of this solution reservoir 124. Alternatively, the membrane may be attached directly to an electrode head 150 that constitutes the release controller in this embodiment. In such a case, release channels 128 may pass through the electrode 150 and end in connection with the membrane.

Upon a stimulation occasion, the channels 132 embedded in the membrane or release surface 110 are temporary opened, causing outflux of high concentrated ionic agent solution to the outside of the release surface 110. The amount of released ionic agent 140 is selected and controlled by the number of channels 132 provided in the release surface 110 and the opening time of these channels 132.

In a preferred implementation, the channels 132 are protein channels or pores having specificity for potassium ions. There are vastly different potassium ion channel types naturally present in different cell types in eukaryotic, eubacterial and archael cells. The potassium channels 132 used according to the present invention are preferably so-called voltage-gated potassium channels 132. The opening and closure mechanism of such channels 132 is made dependent on an applied voltage. Some of these channels 132 are closed at negative transmembrane potentials (i.e. resting potentials) and then opens at positive potentials, whereas other channels 132 opens at potentials more negative than the resting membrane potential. Most such potassium channels 132 are open only for a limited period of time as they will become inactivated for longer activation potential periods. Correspondingly, when the membrane potential returns to the resting state, the channels 132 transit from the open (conducting) or inactivated (non-conducting) state back to the closed (non-conducting) state. The opening time and thereby the amount of potassium ions passing through the channels 132 can be controlled by the applied voltage (voltage level, application time and application profile).

Once the voltage is stepped back to the resting potential, the channels 132 will most often conduct once more, but in an opposite direction, i.e. potassium ions present extracellularly will be transported by the channels 132 into the interval space or cavity 127. These ions can therefore be recycled and used in subsequent tissue stimulations, In this embodiment, the tissue stimulating device 100 comprises an electrode 150 for applying a channel opening voltage (pulse) at a stimulation occasion to cause an opening of the channels 132 in the release surface 110 and an outflow of ionic agents 140 from the internal cavity 127 to the outside of the release surface 110. The actual voltage level applied by the electrode 150, the application time and the application profile (voltage pulse or step-wise increase/decrease in voltage levels) is selected based on the type of ion channel 132 employed, the concentration of the ionic agent solution in the internal cavity 127 and the amount of ionic agent 140 required for initiating a tissue stimulation.

There are several possible ionic agent channels 132 known in the art and the skilled person can non-inventively select one of these for use according to the present invention. In such a case, the channel selection is preferably performed based, at least partly, on the gating mechanism of the channels 132 to find a channel 132 that opens at pre-selected applied potentials and stays open long enough for enabling a sufficient amount of ionic agent 140 to pass through the channels 132 before the channels 132 become inactivated or closed. In addition, the ionic agent channels 132 are preferably from an allogeneic source, i.e. the channel 132 are naturally expressed and found in the species into which the tissue stimulating device 100 is to be implanted. As a consequence, if the intended patient is a human, the agent channels 132 are preferably found in any human cells. This reduces the risk of rejection reactions that might occur if channel proteins from a non-allogeneic source are employed.

Figure 10:
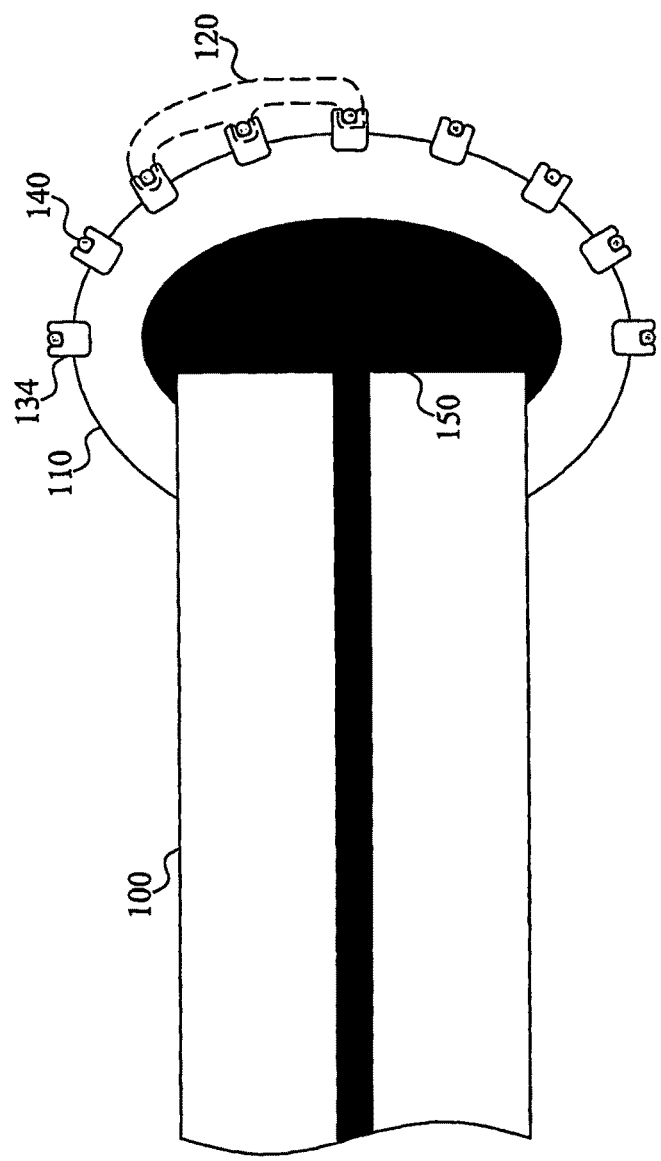
FIG. 10 illustrates a portion of a tissue stimulating device according to still another embodiment of the present invention.

FIG. 10 is a schematic illustration of an end portion of a tissue stimulating device 100 according to still another embodiment of the present invention. In this embodiment, the release surface 110 is provided with multiple carrier molecules 134 having a capacity of reversibly binding to the ionic agent 140. The carrier molecules 134 are typically selected from proteins having reversible ionic agent binding capacity, preferably reversibly potassium ion binding capacity. In this case, the carrier molecules 134 can be embedded in a phospholipid membrane or other membrane describe above in connection with FIG. 9.

In a preferred implementation, the reversible binding of these carrier molecules 134 to the ionic agent 140 of the invention is dependent on a potential applied by a voltage electrode 150. Thus, at a certain resting potential, the carrier molecules 134 bind to ionic agent 140 present in the surrounding medium or provided from internal agent reservoirs (not illustrated). At a stimulation occasion, the electrode 150 applies a voltage over the release surface 110 causing the carrier molecules 140 to release any bound ionic agents 140. As a consequence, the concentration of unbound ionic agent 140 outside the release surface 110 increases and tissue stimulation is triggered. Once the applied voltage (pulse) ceases the carrier molecules 134 will undergo a conformation change so that they once more bind to ionic agent 140 taken from the surrounding medium.

It is anticipated by the invention that it might be necessary to replenish ionic agents 140 that dissociate from the vicinity of the release surface 110 once released from the carrier molecules 134. As a consequence, the tissue stimulating device 100 preferably comprises at least one internal agent reservoir (solid agent reservoir and/or solution agent reservoir) that can release ionic agent 140 outside of the device 100, where the agents 140 become bound by the carrier molecules 134 having empty binding sites.

It is preferred if the carrier molecules 134 each have multiple ionic agent binding sites to thereby reduce the number of such molecules 134 required for releasing a sufficient amount of ionic agent 140 for causing a stimulation of a nearby tissue.

Examples of carrier molecules 134 that can be used according to the present invention include Valinomycin that selectively and reversibly binds to potassium ions, dicarboxylic acid-dicarboxamide macrocycles that can be used as carrier for potassium and calcium ions (*Proc. Natl. Acad. Sci. USA*, Vol. 80, pp. 6426-6428, 1983) and calciphorin that can be used as a $Ca^{2+}$ carrier (*Proc. Natl. Acad. Sci. USA*, Vol. 75(5), pp. 2125-2129, 1978).

In this embodiment, the ionic agent 140 bound to the carrier molecules 134 collectively constitutes the agent reservoir 120 or a part of the reservoir 120. The tissue stimulating device 100 can also comprise a solid agent reservoir 122 in addition to the solution reservoir 124 for replenish ionic agents released through the channels 132 and not being recycled. The operation of these reservoirs is similar to what has been described in the foregoing.

The present invention also encompasses a combination of the two embodiments disclosed in FIGS. 9 and 10. In such a case, the membrane defining the release surface can include both (voltage-gated) ionic agent channels and carrier molecules reversibly binding (dependent on a membrane potential level) the ionic agent. In such a case, the agent channels and carrier molecules are selected to open and release ionic agent, respectively, at substantially the same transmembrane potential. For example, the ionic agent channels will open and conduct ionic agents and the carrier molecules will release bound ionic agents at transmembrane potentials more positive (or negative) than the resting potential state.

It is anticipated by the present invention that the tissue stimulating device may be equipped with multiple release surfaces that then can be used for stimulating different parts of a target tissue or different neighbouring tissues. In such a case, each release surface can have a dedicated reservoir, channel and release system or one or more such systems shared between the release surfaces.

The body of the tissue stimulating device of the invention can be made of any biocompatible, non-toxic and stable material. Examples include different plastics, elastomers, glasses, ceramics, metals and metal alloys, including titanium, steel and platinum metals and alloys commonly used in the art.

In a preferred implementation, the tissue stimulating device has a general elongated shape. It is often preferred that the overall size of the device is minimized to reduced the impact the device has to the surrounding tissues and organs when implanted/inserted into the body of a subject, preferably a mammalian subject and more preferably a human subject. The size and also shape of the device may of course be adapted to the actual implantation site and the tissue to be stimulated.

The different agent release arrangements described above and disclosed in the FIGS. 1, 2, 3, 6, 8-10 are all able to release a selected amount of the ionic agent within a short period of time. Thus, the ionic agent release from the tissue stimulating device can be regarded as instantaneous or immediate in terms of delivering a selected quantity of the ionic agent at the outside of the release surface during a very short time period. The reason for this quick agent release is that if the release of a selected amount of the ionic agent takes place over a considerable period of time, released ionic agent will disperse into the surrounding body fluids and tissues. As a consequence, it might then be difficult to attain a sufficient large local concentration (quantity) of the ionic agent close to the tissue to be stimulation or unnecessary large quantities of the ionic agent must be released for attaining stimulation induction. In a preferred implementation, the agent release arrangements of the invention are able to release an amount of the ionic agent sufficient for triggering a stimulation of an adjacent tissue within a period of time in the interval 1 μs (or shorter) to 1 s. It is generally sufficient, if the release procedure lasts for one or few tens of milliseconds up to one or few hundreds of milliseconds or shorter.

A preferred ionic agent according to the present invention is potassium ions. These ions significantly contribute to the membrane potential when tissue cells are at a resting (non-stimulated) state. Hence, a sudden change in the $K^+$ concentration in the vicinity of the cells will induce changes to the permeability of certain ions through the cell membranes. For example, in heart tissue a high extracellular $K^+$ concentration will induce activation of sodium channels and lead to a contraction (stimulation) of the heart tissue.

If it is assumed that the membrane is permeable to both sodium and potassium ions, the transmembrane potential can roughly be calculated by the following expression:

$$V_{membrane} = 61.5 \log\left(\frac{P_K[K_0] + P_{Na}[Na_0]}{P_K[K_i] + P_{Na}[Na_i]}\right) \quad (1)$$

where $V_{membrane}$ is the transmembrane potential in millivolts (mV), $P_K$ is the membrane permeability to potassium ions, $P_{Na}$ is the membrane permeability to sodium ions, $[K_0]$ is the extracellular concentration of potassium ions, $[K_i]$ is the intracellular concentration of potassium ions, $[Na_0]$ is the extracellular concentration of sodium ions, and $[Na_i]$ is the intracellular concentration of sodium ions.

By assuming that the membrane is mainly permeable to potassium (resting non-stimulated state) the equation 1 can be reduced to:

$$V_{membrane} = 61.5 \log\left(\frac{[K_0]}{[K_i]}\right) \quad (2)$$

The intracellular potassium ion concentration is about 150 mM in most tissue cells of the human body. In heart tissue, the sodium channels activates at a transmembrane potential of about −65 mV. As a consequence, a stimulation of heart tissue requires addition of potassium ions to achieve a transmembrane potential of about −65 mV. This amounts to about 13 mM using the above-given numbers and equation 2.

This means that if the concentration of potassium ions increases to about 13 mM or more outside the tissue cells, the sodium channels in the cell membranes will open and a stimulation of the heart cell is triggered.

In an exemplified embodiment, the release surface of the tissue stimulating device may have a geometric area of, for example, 3.5 mm$^2$ and the distance between the release surface and the cell membranes is about 100 μm. In order to achieve a potassium ion concentration of 13 mM at this volume between the release surface and the cell membranes, merely about 0.18 μg potassium ions are required.

As the tissue stimulating device of the invention can have varying dimensions depending on the operation site and different tissues will typically require varying amounts of the ionic agent (K$^+$) for stimulation triggering, the above-given number of 0.18 μg potassium ion should mainly be regarded as an illustrative amount of minimum potassium ion quantities. The expression given below can be used by the person skilled in the art for determining minimum potassium ion quantities required for triggering tissue stimulation:

$$m_K = 32.1 \times A \times d \times [K_i] \times 10^{\frac{V_{membrane}}{61.5}} \quad (3)$$

where $m_K$ (is the mass potassium ions (in grams) required for tissue stimulation, A is the release surface area (in dm$^2$), d is the distance between release surface and the tissue (in dm), $[K_i]$ is the intracellular concentration of potassium ions in the tissue cells at a resting (non-stimulated) state (in molars) and $V_{membrane}$ is the membrane potential at which tissue stimulation is trigger (in millivolts). Thus, given these parameters that depend on the actual device design and the tissue to be stimulated, the minimum amount of potassium ions can be determined.

A saturated aqueous KCl solution comprises about 36 g KCl per 100 g H$_2$O (in room temperature), which amounts to about 171 g K$^+$ per liter solvent. As a consequence, using such a saturated KCl solution would merely require release of about 1.1 nl solution for achieving the desired potassium ion concentration and stimulation triggering if 0.18 μg K$^+$ induces stimulation as above. These example numbers illustrate that it is possible to use diluted KCl aqueous solutions and still only requiring release of small volumes of the solution at each stimulation occasion. For example, if a release volume of about 1 μl is desirable, then the release KCl solution could have a KCl concentration of about 950 lower than the saturation limit, i.e. about 38 mg KCl per 100 g H$_2$O solvent.

According to the present invention, if potassium in the form of KCl is employed as ionic agent in an aqueous solution, the KCl concentration in the solution can be from saturation solution down a dilution of one or few ten thousands, e.g. a dilution of about one or few hundreds up to a dilution of one or few thousands as compared to the saturation concentration.

The corresponding concentrations and amounts of other ionic agents besides potassium ions to use according to the present invention for trigger tissue stimulation can non-inventively be determined from the Goldman-Hodgkin-Katz equation presented below:

$$V_{membrane} = \frac{RT}{F} \ln \left( \frac{\sum_i^N P_{M_i^+}[M_i^+]_{out} + \sum_j^M P_{A_j^-}[A_j^-]_{in}}{\sum_i^N P_{M_i^+}[M_i^+]_{in} + \sum_j^M P_{A_j^-}[A_j^-]_{out}} \right) \quad (4)$$

where $V_{membrane}$ is the membrane potential, $P_{ion}$ is the membrane permeability for that ion, $[ion]_{out}$ is the extracellular concentration of that ion, $[ion]_{in}$ is the intracellular concentration of that ion, R is the ideal gas constant, T is the temperature in Kelvin and F is Faraday's constant. $M_i^+$ refers to a cation and $A_j^-$ denotes an anion.

Figure 11:
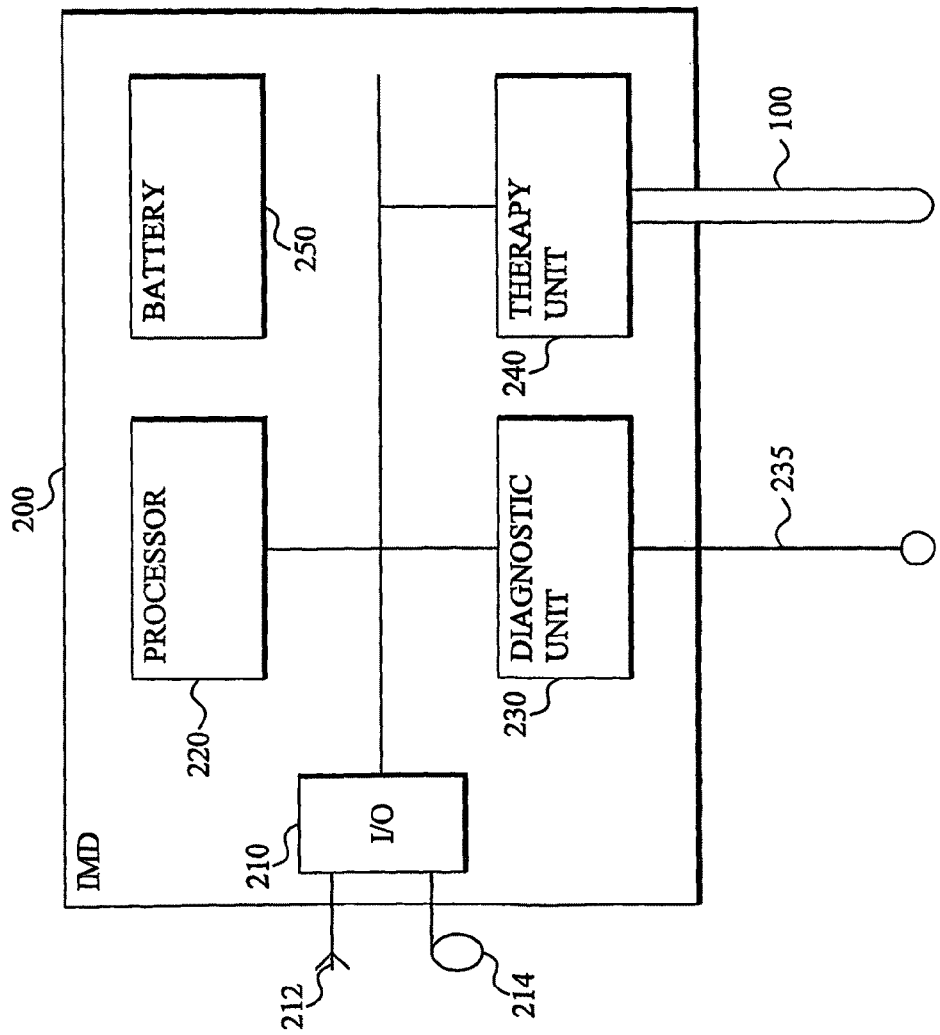
FIG. 11 illustrates an implantable medical device according to an embodiment of the present invention.

FIG. 11 is a schematic block diagram illustrating an implantable medical device (IMD) 200 equipped with a tissue stimulating device 100 according to the present invention. The IMD 200 may be a pacemaker, implantable cardioverter or implantable defibrillator for applying heart therapy in the form of heart stimulation in a patient in need thereof. The IMD 200 needs not necessarily be employed for heart therapy but can likewise by used for stimulating other body tissues, e.g. be a neurological stimulator.

The IMD 200 generally includes an input and output (I/O) unit 210 for conducting wireless communication with an external unit, e.g. a programmer. This I/O unit 210 includes functionalities for processing incoming and outgoing data messages, including modulator/demodulator and coder/decoder functionality. The I/O unit 210 is further preferably connected to an antenna arrangement 212 used for transmitting and receiving radio packets to and from the external unit, respectively. However, the I/O unit 210 could also or alternatively use other forms of wireless techniques than radio frequency transmissions when communicating with the external device. The I/O unit 210 could for example use an inductive antenna 214 for external wireless communication.

In a preferred embodiment of the invention, the IMD 200 also comprises a diagnostic unit 230 connected to a sensor or probe 235 used for collecting physiological data and measuring physiological parameters in the body of the patient in which the IMD 200 is implemented. This parameter can be a parameter measured in the blood system of the user, such as blood glucose level, a parameter measured in connection with an organ or tissue, such as intracardiac signal, pulmonary/respiratory activity, brain and/or spinal activity, kidney-related parameters, liver-related parameters, etc, or any other parameter that can be of diagnostic value for determining a need for a tissue stimulation. The collected and measured physiological parameter data is then forwarded to the processor 220 for data processing. The processor 220 will determine, based on the collected physiological data, whether there is a need for tissue stimulation. For example, collected data of the operation of a patient's heart may indicate heart arrhythmia and a need for heart stimulation. In such a case, the processor 220 generates a stimulation signal that is forwarded to a therapy unit 240 connected to the tissue stimulating device 100. The therapy unit 240 could simply forward the stimulation signal to the release controller of the tissue stimulating device 100. Alternatively, the therapy unit 240 first performs signal processing before forwarding the processed signal to the release controller. In either case, the release controller triggers the agent releaser of the tissue stimulating device 100 to release a selected amount of the ionic agent from an agent reservoir to the outside of the release surface in the device 100, leading to a tissue stimulation.

The IMD 200 is also typically equipped with a battery 250 or other power source for providing the power necessary for driving the I/O unit 210, processor 220, diagnostic unit 230 with probe 235 and therapy unit 240 with tissue stimulating device 100.

The tissue stimulating device 100 of the invention may constitute a separate device that is connectable to the IMD 200 and the therapy unit 240. Alternatively, the device 100 constitutes an internal part of the IMD 200 and cannot be reversibly be detached therefrom. In such a case, the relatively larger size of the IMD 200 can be used while reducing the size of the tissue stimulating device 100. For example, the agent reservoir and elements of the agent releaser and/or release controller can be physically implemented in the IMD body 200, while the reservoir channels or release channels run through the length of the stimulating device 100. However, in this latter case, the whole IMD 200 may be regarded as a tissue stimulating device as defined by the present invention that in addition to the actual stimulation functionality also can include communication, processing and diagnosing functions. It also anticipated by the present invention that the sensor functionality of the probe 235 may be housed within or at least connected to the body of the tissue stimulating device 100.

The units 210, 220, 230 and 240 of the IMD 200 can be provided as hardware, software or a combination of hardware and software.

Figure 12:
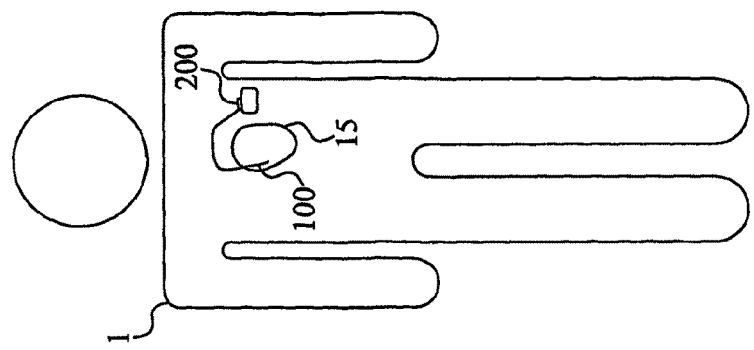
FIG. 12 illustrates a patient equipped with an implantable medical device according to an embodiment of the present invention.

FIG. 12 schematically illustrates an IMD 200 with a tissue stimulating device 100 of the invention implanted in a patient or subject 1 in need thereof. In the figure, the IMD 200 is illustrated as a device that monitors and/or provides therapy to the heart 15 of the patient 1, such as a pacemaker, defibrillator or cardioverter. As a consequence, the tissue stimulating device 100 is ending with its release surface close to the heart 15 to be stimulated.

Figure 13:
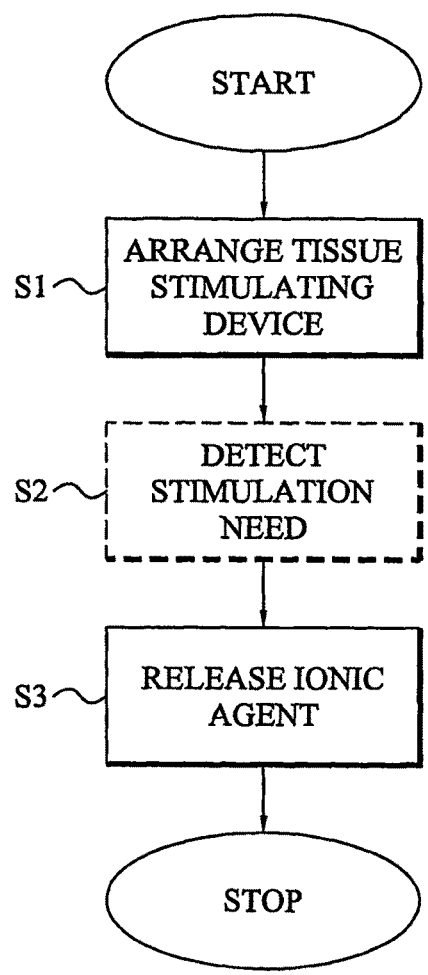
FIG. 13 is a flow diagram illustrating a tissue stimulating method according to an embodiment of the present invention.

FIG. 13 is a flow diagram of a method of stimulating a tissue according another aspect of the invention. The method starts in step S1 where the tissue stimulating device of the invention is arranged adjacent to the tissue to be stimulated. In this arrangement step S1, the at least one release surface of the device is brought close to or even in contact with the tissue wall. Generally, the smaller distance between the release surface and the tissue wall, the faster and more efficient (requires less ionic agent) tissue stimulation. The stimulating method of the invention can be performed both in vitro and in vivo. In the former case, the tissue stimulating device is arranged close to a tissue provided in culture dish or other laboratory vessel. For example, the tissue stimulating device could then be used for stimulating nerve, muscle or heart tissue cultured in vitro. In the latter case, the tissue stimulating device is implanted into the body of a subject, preferably mammalian subject and more preferably a human subject, in need of tissue stimulation.

In a next optional step S2, a need for stimulation is detected. This step S2 is typically performed in vivo when the tissue stimulating device is transplanted into the subject body as a part of or connected to an IMD. In such a case, a diagnostic functionality of the IMD can be used for monitoring different physiological parameters in the body and determine whether a need for tissue stimulation is present.

A next step S3 releases a selected amount of the ionic agent from the release surface of the tissue stimulating device to the outside of the tissue. There this local increase in the ionic agent concentration causes a stimulation of the tissue by opening of ion channels in the tissue cell membranes and a cell depolarization.

This agent releasing step S3 can be performed in response to the detection of a stimulation need in step S2. Furthermore, the release step S3 may be performed at multiple separate time instances depending on whether the stimulation need once more exists. Otherwise the method ends.

Although modifications and changes may be suggested by those skilled in the art, it is the intention of the inventors to embody within the patent warranted heron all changes and modifications as reasonably and properly come within the scope of their contribution to the art.

We claim:

1. A tissue stimulating device comprising:
   a release surface adapted for arrangement adjacent to a tissue to be stimulated;
   an agent reservoir comprising an ionic agent;
   an agent releaser for releasing an amount of said ionic agent from said agent reservoir to an outside of said release surface for stimulating said tissue;
   wherein said agent reservoir is a solution agent reservoir comprising said ionic agent in an aqueous solution;
   a release reservoir comprising said ionic agent in said aqueous solution and having an inner reservoir volume that is smaller than an inner reservoir volume of said solution agent reservoir;
   a first transport channel connected in a first end with said solution agent reservoir and in a second end with said release reservoir; and
   a second transport channel connected in a first end with said release reservoir and in a second end with said release surface.

2. The tissue stimulating device according to claim 1, further comprising a release controller for controlling said agent releaser to release a selected amount of said ionic agent for stimulating said tissue.

3. The tissue stimulating device according to claim 2, wherein said selected amount of said ionic agent comprises an amount of said ionic agent sufficient for generation of a depolarization of cells of said tissue.

4. The tissue stimulating device according to claim 2, wherein said release controller is configured to control said agent releaser to release a selected amount of said ion agent resulting in an instantaneous increase in local ion concentration at said outside of said release surface, where said instantaneous increase in local ion concentration is sufficient for stimulating said tissue.

5. The tissue stimulating device according to claim 2, wherein said agent releaser comprises a carrier molecule provided in said release surface, which carrier molecule reversibly binds to said ionic agent with a reversible binding that is dependent on an applied potential, and said release controller comprises an electrode for changing a potential experienced by said carrier molecule and causing said carrier molecule to release a selected amount of said ionic agent at said outside of said release surface.

6. The tissue stimulating device according to claim 1, wherein said ionic agent is a potassium ion.

7. The tissue stimulating device according to claim 6, wherein said release controller is configured to control said agent releaser to release an amount $m_K$ of said potassium ion to said outside of said release surface:

$$m_K = 32.1 \times A \times d \times [K_i] \times 10^{-\frac{V_{membrane}}{61.5}}$$

where $m_K$ is a mass of potassium ions in grams required for tissue stimulation, A is an area of said release surface in dm2, d is a distance in dm between said release surface and said tissue, [Ki] is an intracellular concentration of potassium ions in molars in cells of said tissue at a resting state and $V_{membrane}$ is a membrane potential in mV at which tissue stimulation is trigger for said tissue.

8. The tissue stimulating device according to claim 6, wherein said agent reservoir comprises said potassium ion in solid form.

9. The tissue stimulating device according to claim 8, wherein said agent reservoir comprises a salt comprising said potassium ion.

10. The tissue stimulating device according to claim 9, wherein said salt is selected from the group consisting of potassium chloride and potassium acetate.

11. The tissue stimulating device according to claim 6, wherein said agent releaser comprises voltage-gated potassium channels provided in said release surface and said release controller comprises an electrode for changing a potential experienced by said voltage-gated potassium channels and opening said voltage-gated potassium channels to release a selected amount of said potassium ion to said outside of said release surface.

12. The tissue stimulating device according to claim 1, wherein said release surface is configured to interact with said tissue selected from the group consisting of heart tissue, muscle tissue and nerve tissue.

13. The tissue stimulating device according to claim 1, wherein said first and second channels are relatively configured to cause a flow resistance of said aqueous solution through said first transport channel to be larger than a flow resistance of said aqueous solution through said second transport channel.

14. The tissue stimulating device according to claim 1, wherein said agent releaser comprises a pulse generator for applying a mechanical pulse onto said release reservoir and pushing a selected amount of said amount of said aqueous solution from said release reservoir through said second transport channel to said outside of said release surface.

15. The tissue stimulating device according to claim 14, wherein said pulse generator comprises a piezoelectric element connected to an outside surface of said release reservoir.

16. The tissue stimulating device according to claim 1, further comprising a pressure source that exerts a flow drive pressure onto said aqueous solution directed from said solution agent reservoir and into said first transport channel.

17. The tissue stimulating device according to claim 16, wherein said pressure source comprises:
a semi-permeable membrane in fluid connection with an outside of said tissue stimulating device and being permeable to a fluid but impermeable to said ionic agent; and
a fluid channel connected in a first end with said semi-permeable membrane and in a second end with said solution agent reservoir, wherein an arising osmotic pressure over said semi-permeable membrane causes said flow drive pressure.

18. A tissue stimulating device comprising:
a release surface adapted for arrangement adjacent to a tissue to be stimulated;
an agent reservoir comprising an ionic agent; and
an agent releaser for releasing an amount of said ionic agent from said agent reservoir to an outside of said release surface for stimulating said tissue;
wherein said agent reservoir comprises:
a solid agent reservoir comprising said ionic agent in solid form; and
a solution agent reservoir in fluid connection with solid agent reservoir and comprising said ionic agent in an aqueous solution.

19. The tissue stimulating device according to claim 18, wherein said solid agent reservoir comprises an ionic-agent-containing material that degrades at a determined rate to keep a selected target concentration of said ionic agent in said aqueous solution of said solution agent reservoir.

20. A tissue stimulating device comprising:
a release surface adapted for arrangement adjacent to a tissue to be stimulated;
an agent reservoir comprising an ionic agent;
an agent releaser for releasing an amount of said ionic agent from said agent reservoir to an outside of said release surface for stimulating said tissue; and
an ionic agent exchange membrane in fluid connection with said agent reservoir through a conduit and adapted for fluid connection with a body fluid and for enriching said ionic agent from said body fluid, and wherein said enriched ionic agent is forwarded to said agent reservoir through said conduit.

21. An implantable medical device comprising:
a tissue probe adapted for arrangement adjacent to a tissue and for detection of a need of stimulating said tissue;
a tissue stimulating device comprising a release surface adapted for arrangement adjacent to said tissue, an agent reservoir comprising an ionic agent, an agent releaser for releasing an amount of said ionic agent from said agent reservoir to an outside of said release surface, and an ionic agent exchange membrane in fluid connection with said agent reservoir through a conduit and adapted for fluid connection with a body fluid and for enriching said ionic agent from said body fluid, and wherein said enriched ionic agent is forwarded to said agent reservoir through said conduit; and
said release surface releasing, in response to said tissue probe detecting a need of tissue stimulation, a selected amount of ionic agent from said agent reservoir of said tissue stimulating device to an outside of said release surface for stimulating said tissue.

22. A method for stimulating tissue in vitro or in vivo, said method comprising the steps of:
arranging a release surface adjacent to tissue to be stimulated;
storing an ionic agent in an agent reservoir in communication with said release surface;
supplying a selected amount of said ionic agent from said agent reservoir to said release surface and releasing said selected amount of ionic agent into said tissue from an outside of said release surface to stimulate said tissue; and
enriching said ionic agent from said body fluid by an ionic agent exchange membrane in fluid connection with said agent reservoir through a conduit and adapted for fluid connection with a body fluid, wherein said enriched ionic agent is forwarded to said agent reservoir through said conduit.

23. A method for stimulating tissue in vivo, said method comprising the steps of:
arranging a tissue probe in vivo, adjacent to tissue to be stimulated;
with said tissue probe, detecting a need to stimulate said tissue;
arranging a release surface in vivo adjacent to said tissue;
storing an ionic agent in an agent reservoir in communication with said release surface, wherein said agent reservoir has a solid agent reservoir and a solution agent reservoir, wherein said solid agent reservoir comprises said ionic agent in solid form, wherein said solution agent reservoir is in fluid connection with said solid agent reservoir, and wherein said solution agent reservoir comprises said ionic agent in an aqueous solution; and upon detection of said need for stimulating said tissue by said tissue probe, automatically releasing a selected amount of said ionic agent from said agent reservoir to an outside of said release surface to stimulate said tissue.

* * * * *